United States Patent [19]

Sikinami et al.

[11] Patent Number: 5,017,377
[45] Date of Patent: May 21, 1991

[54] CONTROLLED RELEASE INSECT PEST REPELLENT

[75] Inventors: Yasuo Sikinami; Kunihiro Hata; Masaki Yasuhara, all of Osaka, Japan

[73] Assignee: Takiran Co., Ltd., Osaka, Japan

[21] Appl. No.: 429,428

[22] Filed: Oct. 31, 1989

[30] Foreign Application Priority Data

Oct. 31, 1988 [JP] Japan .................. 63-274662
Mar. 22, 1989 [JP] Japan .................. 1-69491

[51] Int. Cl.$^5$ ............ A01N 25/08; A61K 31/74; A61K 31/745
[52] U.S. Cl. ................. 424/409; 424/78; 424/83; 514/918; 514/919
[58] Field of Search ............ 514/918, 919; 424/78, 424/83, 409

[56] References Cited

U.S. PATENT DOCUMENTS

| 3,873,725 | 3/1975 | Skinner et al. | 424/342 |
|---|---|---|---|
| 3,876,762 | 4/1975 | Rabussier | 424/78 |
| 3,991,213 | 11/1976 | Mitsubayashi | 514/134 |
| 4,195,075 | 3/1980 | Miller | 424/16 |
| 4,536,388 | 8/1985 | Pearce, III | 924/78 |
| 4,543,367 | 9/1985 | Rutherford et al. | 424/78 |
| 4,548,764 | 10/1985 | Munteanu et al. | 424/9 |
| 4,816,248 | 3/1989 | Wilson | 424/84 |
| 4,853,413 | 8/1989 | Katz et al. | 514/426 |

FOREIGN PATENT DOCUMENTS

| 0282951 | 9/1988 | European Pat. Off. . |
|---|---|---|
| 57-106603 | 7/1982 | Japan . |
| 60-199804 | 9/1985 | Japan . |
| 1326825 | 8/1973 | United Kingdom . |

Primary Examiner—Lester L. Lee
Assistant Examiner—Carmen B. Pili-Curtis
Attorney, Agent, or Firm—Sughrue, Mion, Zinn, Macpeak & Seas

[57] ABSTRACT

A controlled release insect pest repellent comprising p-menthane-3,8-diol blended with an ethylene/vinyl acetate copolymer is disclosed. This controlled release insect pest repellent can show continuous controlled release of the repellent component, i.e., p-menthane-3,8-diol, for a prolonged period of time so as to effectively exterminate insect pests.

4 Claims, No Drawings

CONTROLLED RELEASE INSECT PEST REPELLENT

FIELD OF THE INVENTION

This invention relates to a controlled release insect pest repellent. More particularly, it relates to a controlled release insect pest repellent which is prepared by blending p-menthane-3,8-diol having a repellent effect on insect pests with a specific base having an appropriately controlled affinity therefore so as to slowly volatilize and release the p-menthane-3,8-diol from the surface of the base for a prolonged period of time.

BACKGROUND OF THE INVENTION

It has been known that p-menthane-3,8-diol has a repellent effect on insect pests such as the mosquito, slug, millipede, night crawler and flea (see H. Nishimura, J. Mizutani, T. Umino & T. Kurihara, 6th Intern. Congr. Pesticide Chem., Abstracts 2D/E-07, Ottawa, Canada, Aug. 10-15th (1986); H. Nishimura, Eucalyptus as Future Biosource, and Biotechnology and Bioscience Thereof, Uchidarokakuho (1987); H. Nishimura, T. Nakamura & J. Mizutani, Phytochemistry, 23, 2777 (1984); H. Nishimura, Fragrance Journal, No. 75, 160 (1985); and H. Nishimura, K. Kaku, T. Nakamura, Y. Fukazawa & J. Mizutani, Agric. Biol. Chem., 46, 319 (1982)). The p-menthane-3,8-diol involves structural isomers and optical isomers, namely, (+)-cis-p-menthane-3,8-diol, (−)-cis-p-menthane-3,8-diol, (+)-trans-p-menthane-3,8-diol and (−)-trans-p-menthane-3,8-diol. Each substance has a melting point ranging from 57 to 60° C. It is in the form of a solid at room temperature but has a volatility in this state. Thus, it can exert the repellent effect on insect pests under certain atmosphere. When p-menthane-3,8-diol is not blended with a base but used as such, however, it exhibits volatility even in the form of a solid at room temperature, as described above, and the volatilization rate thereof cannot be controlled, which brings about serious waste.

In contrast thereto, JP-A-60-199804 (the term "JP-A" as used herein means a "published unexamined Japanese patent application") describes "A collar to which a resin impregnated with a repellent such as p-menthane-3,8-diol (PM) is used for pet such as dog". However, no particular resin is not specified therein. The addition of PM to resins, other than some limited ones, would be useless because of the following facts: (1) the added PM bleeds out onto the surface of the resin, which makes it impossible to control the volatilization rate thereof; or (2) the added PM is enclosed within the resin and can hardly volatilize.

When p-menthane-3,8-diol is added to a base resin comprising a single homopolymer, it is impossible to slowly volatilize and release the p-menthane-3,8-diol within an effective range from the surface of the base resin for a prolonged period of time, namely, so-called controlled release. The reason is as follows.

When a volatile substance is uniformly contained in a base material, the volatile substance present on the surface of the base material would volatilize into the atmosphere depending on its inherent vapor pressure. As a result, the concentration of the volatile substance on the surface of the base material differs from that at the core part, thus forming a concentration gradient. Then, the volatile substance present at the core part would slowly migrate into the surface layer and then volatilize into the atmosphere. Thus, the volatile substance within the base material would continuously volatilize into the atmosphere while maintaining the above flow. In order to slowly release a volatile substance in an appropriate amount for a prolonged period of time, therefore, it is required that the volatile substance is uniformly contained in a base material at a concentration allowing the formation of a continuous layer thereof; and that the migration rate of the volatile substance in the base material is controlled in such a manner that the volatile substance can volatilize at an appropriate volatilization rate.

The affinity of the base material for the volatile substance closely relates to the concentration and migration rate of the volatile substance. Thus, it is difficult to slowly release the volatile substance in an appropriate amount unless the affinity is appropriately controlled. When the affinity is excessively low, the compatibility between these substances becomes low. Thus, the volatile substance can be added to the base material only in a small amount. In this case, therefore, it is difficult to slowly release an appropriate amount of the volatile substance for a long time. When the affinity is excessively high, on the other hand, the high compatibility between these substances makes the migration rate of the volatile substance in the base material extremely low. In this case, therefore, it is difficult to volatilize an appropriate amount of the volatile substance.

When the base resin to which PM is to be added is a homopolymer, it is impossible to appropriately control the affinity of the base resin for PM, which causes the following problems. When the affinity of the homopolymer for PM is low, PM can be added only in a small amount. Thus, it is difficult to control the repellent effect of PM for a long time. When the affinity of the homopolymer for PM is high, on the other hand, the migration rate of PM becomes extremely low. Thus, it is difficult in this case to release PM in a satisfactory amount for achieving the aimed repellent effect.

SUMMARY OF THE INVENTION

It is an object of the present invention to provide a controlled release insect pest repellent which can slowly volatilize and release p-menthane-3,8-diol in an effective amount for exerting a repellent effect on insect pests for a prolonged period of time.

It is another object of the present invention to provide a controlled release insect pest repellent having excellent molding properties.

The present inventors have conducted extensive studies on the formation of a controlled release system for p-menthane-3,8-diol. As a result, they found that the above object can be achieved through the production of a controlled release insect pest repellent by blending p-menthane-3,8-diol to an ethylene/vinyl acetate copolymer.

Other objects, features and advantages of the present invention will be apparent from the following description.

The term "repellent" used herein means a molded product having a repellent effect.

DETAILED DESCRIPTION OF THE INVENTION

As described above, the p-menthane-3,8-diol to be used in the present invention involves four isomers, namely, (+)-cis-p-menthane-3,8-diol, (−)-cis-p-menthane-3,8-diol, (+)-trans-p-menthane-3,8-diol and (−)-trans-p-menthane-3,8-diol. Each isomer has a melting point ranging from 57 to 60° C. and is present in the form of a solid at room temperature.

It is possible to use each p-menthane-3,8-diol isomer alone as a solid. However, it is preferable to use a mixture of cis- and trans-isomers. When a small amount of a p-menthane-3,8-diol isomer is blended with a base comprising an ethylene/vinyl acetate copolymer in the form of a solid at room temperature, the isomer is frequently non-continuously dispersed in the base. Thus, a continuous layer can be hardly formed in this case. When a cis-isomer is used together with a trans-isomer at a specific ratio, on the other hand, the mixture, which is in the form of a liquid, would be continuously dispersed in the base material and thus form a continuous layer, even in a small amount. As a result, a more stable controlled release system may be more readily achieved. A liquid mixture of isomers can be obtained by mixing (+)-cis-p-menthane-3,8-diol with (+)-trans-p-menthane-3,8-diol, (+)-cis-p-menthane-3,8-diol with (−)-trans-p-methane-3,8-diol, (−)-cis-p-menthane-3,8-diol with (+)-trans-p-menthane-3,8-diol and (−)-cis-p-menthane-3,8-diol with (−)-trans-p-menthane-3,8-diol, each at a ratio of one component of from 15 to 85%, preferably 30 to 70% (by weight, the same will apply hereinafter). This fact has been found out by the present inventors. When each isomer is to be used alone, therefore, it is desirable to add an appropriate liquid material so as to facilitate the formation of a continuous layer within the base.

The content of the p-menthane-3,8-diol may appropriately range from approximately 5 to 30% of the total composition. When it is smaller than 5%, it becomes difficult to control a satisfactory repellent effect for a long time. On the other hand, a content of p-menthane-3,8-diol exceeding 30% might cause some problems in molding properties or cost. It is still more preferable to adjust the content of p-menthane-3,8-diol within 10 to 20%.

As described above, it is one of the requirements for the formation of the controlled release system comprising p-menthane-3,8-diol blended in a base that the migration rate of the p-menthane-3,8-diol in the base is controlled so as to give an appropriate volatilization rate thereof. It is required therefore to control the affinity of p-menthane-3,8-diol for the base. It is commonly known that the affinity of a substance for a polymer depends on the solubility parameter (SP). When the SP of a polymer is close to that of a substance, the affinity between these materials is high and thus they are highly compatible. When the SP of a substance considerably differs from that of a polymer, on the contrary, the affinity between them is low and thus they are scarcely compatible.

When a base comprises a single homopolymer, a controlled release system of p-menthane-3,8-diol can be hardly formed, since the affinity cannot be controlled as described above. Accordingly, a polymer having two or more constituting molecule moieties which are different from each other in the affinity for p-menthane-3,8-diol, per molecule, is useful as a base for forming a controlled release system. Suitable examples of such a polymer involve block copolymers, graft copolymers and random copolymers. Further, a blend of a homopolymer having a high affinity for p-menthane-3,8-diol with one having a low affinity therefore may be available. In this case, however, the dissolution properties of the blend would depend on those of each homopolymer. As a result, p-menthane-3,8-diol is dissolved preferentially in a homopolymer having a higher affinity therefore. Thus, the migration rate of the p-menthane-3,8-diol in the polymer layer becomes extremely low. Thus, it is difficult to appropriately control the volatilization of p-menthane-3,8-diol from the surface layer, even though the migration of p-menthane-3,8-diol in the whole system can be controlled on the macro surface at the interface with an incompatible polymer. Accordingly, a sufficient repellent effect can hardly be achieved in this case.

When a block, graft or random copolymer having two or more constituting molecule moieties differing from each other in affinity for p-menthane-3,8-diol per molecule is used as a base, in contrast thereto, the volatilization rate of p-menthane-3,8-diol can be controlled by appropriately adjusting the kinds and composition ratio of the monomer units or the length of each segment. In such a copolymer, the micro-phase separation in a molecule has been achieved and each microdomein is highly dispersed. Therefore, the p-menthane-3,8-diol molecules added thereto are also finely dispersed therein. Thus, the copolymer can exert properties which can never been obtained by physically blending homopolymers. That is, it is possible to appropriately control the compatibility of a copolymer, which comprises a monomer unit whose SP is relatively close to that of p-menthane-3,8-diol (or a segment comprising a continuous phase of a monomer) with a monomer unit whose SP is considerably different from that of p-menthane-3,8-diol (or segment), with p-menthane-3,8-diol so as to achieve the controlled release of the repellent component. Furthermore, the rate of the controlled release can be satisfactorily controlled by adjusting the ratio of, for example, the segments.

As described above, the repellent component p-menthane-3,8-diol is volatile at room temperature. However, it is needless to say that the volatility thereof would increase as temperature increases. Thus, it is undesirable that the base containing the repellent component has a high molding temperature, since the amount of the volatilized repellent component is increased thereby. Accordingly, it is required to select a base material which has as low a molding temperature as possible and yet shows excellent molding properties.

The present inventors have conducted extensive studies to find out a base polymer satisfying the above-mentioned requirements for achieving a controlled release system. As a result, they have found out that an ethylene/vinyl acetate copolymer, ethylene/acrylate copolymer, acrylate/acrylonitrile copolymer, butadiene/acrylonitrile copolymer, ethylene/vinyl alcohol copolymer, partially saponified PVA, polyethylene glycol/polypropylene glycol copolymer, etc., are effective therefore. They have further found out that ethylene/vinyl acetate copolymer is the most suitable among these materials, from the viewpoints of the formation of the aimed controlled release system and molding properties.

Accordingly, the ethylene/vinyl acetate copolymer to be used in the present invention as a base is a polymer which carries two constituting molecule moieties differing from each other in affinity for p-menthane-3,8-diol, i.e., an ethylene unit and a vinyl acetate unit, per molecule. The SP of p-menthane-3,8-diol is 13.8, while those of the ethylene and vinyl acetate units are 8.6 and 11.3, respectively. Namely, the vinyl acetate unit has a relatively high affinity for p-menthane-3,8-diol while the ethylene unit has a relatively low affinity therefore. Thus, it is possible to establish a controlled release system for the repellent component by appropriately controlling the constituting ratio between the ethylene and vinyl acetate units. When the content of the vinyl acetate unit is elevated, for example, a controlled release system having a high affinity for the repellent component as the whole can be obtained, which enables controlled release of the repellent component for a prolonged period of time.

The maximum content of the p-menthane-3,8-diol to be added to the ethylene/vinyl acetate copolymer varies depending on the content of the vinyl acetate unit having a high affinity therefore. Namely, the upper limit of the p-menthane-3,8-diol content increases with an increase in the content of the vinyl acetate unit. When p-menthane-3,8-diol is added at a ratio of, for example, 5%, 10%, 20% and 30% of the total composition, it is required to adjust the lower limit of the content of the vinyl acetate unit in the ethylene/vinyl acetate copolymer to approximately 15%, 25%, 30% and 35%, respectively. As described above, the lower limit of p-menthane-3,8-diol for achieving the aimed effect is 5%. Thus, it is required that the ethylene/vinyl acetate copolymer contains at least approximately 15% of the vinyl acetate unit.

On the other hand, the ethylene/vinyl acetate copolymer shows excellent molding properties when the content of the vinyl acetate unit is approximately 30% or below. When the content thereof exceeds this value, the molding properties of the ethylene/vinyl acetate copolymer are deteriorated, which makes the molding difficult. However, an ethylene/vinyl acetate copolymer containing 30% or more of a vinyl acetate unit can be relatively easily molded by adding another powdery ethylene/vinyl acetate copolymer containing about 50 to 70% of a vinyl acetate unit thereto. The powdery ethylene/vinyl acetate copolymer can be added in an amount up to approximately 30% of the base ethylene/vinyl acetate copolymer. Accordingly, a molded product of an ethylene/vinyl acetate copolymer containing approximately 40% of a vinyl acetate unit can be obtained by adding the maximum amount of the powdery copolymer.

Therefore, the ethylene/vinyl acetate copolymer to be used as a base in the present invention contains the vinyl acetate unit in a content within a range of from approximately 15 to 40%. The controlled release of the p-menthane-3,8-diol at an aimed volatilization rate for a long time can be achieved by varying the content of the vinyl acetate unit within the range as specified above so as to control the affinity thereof for the p-menthane-3,8-diol.

The ethylene/vinyl acetate copolymer may further contain other commonly used resins such as polyvinyl chloride, chlorinated polyethylene or polyethylene, if required.

The p-menthane-3,8-diol may be blended with the ethylene/vinyl acetate copolymer by, for example, (1) adding the p-menthane-3,8-diol to the ethylene/vinyl acetate copolymer under stirring and heating so as to allow the ethylene/vinyl acetate copolymer to absorb the p-menthane-3,8-diol or (2) kneading these materials together on a heated roll, as described below.

Method (1)

(a) When only an ethylene/vinyl acetate copolymer containing 40% or less of a vinyl acetate unit is used as a base resin, the ethylene/vinyl acetate copolymer is stirred by mixer under heating at 30° to 40° C. and then the p-menthane-3,8-diol is added dropwise thereto to allow the copolymer to absorb the p-menthane-3,8-diol.

(b) When the mixture of an ethylene/vinyl acetate copolymer containing 30% or less of a vinyl acetate unit and a powdery ethylene/vinyl acetate copolymer containing about 50 to 70% of a vinyl acetate unit is used as a base resin, the master pellets of both copolymers are prepared using an ordinary granulator, these master pellets are stirred by mixer under heating at 30° to 40° C. and then the p-menthane-3,8-diol is added dropwise thereto to allow the copolymer to absorb the p-menthane-3,8-diol.

Method (2)

(a) When only an ethylene/vinyl acetate copolymer containing 40% or less of a vinyl acetate unit is used as a base resin, the copolymer is kneaded together with the p-menthane-3,8-diol on a heated roll at 50° to 90° C. to obtain a sheet-type product.

(b) When the mixture of an ethylene/vinyl acetate copolymer containing 30% or less of a vinyl acetate unit and a powdery ethylene/vinyl acetate copolymer containing about 50 to 70% of a vinyl acetate unit is used as a base resin, the ethylene/vinyl acetate copolymer containing 30% or less of a vinyl acetate unit is kneaded with the p-menthane-3,8-diol absorbed previously into the powdery ethylene/vinyl acetate copolymer on a heated roll at 50 to 90° C. to obtain a sheet-type product.

The ethylene/vinyl acetate copolymer containing the p-menthane-3,8-diol thus obtained may be molded into any form, for example, pellets, sheet, net or rod by a molding machine commonly used in the plastics industry. In this case, various additives such as colorants, fillers or plasticizers may be added thereto, if required.

In the present invention, p-menthane-3,8-diol may be used together with other vegetable essential oils having a repellent effect as repellent components. Examples of these vegetable essential oils include peppermint oil, laurel oil, pine oil, eucalyptus oil, citronella oil, pennyroyal oil, cedar oil, rutaceae oil, white cedar oil, lavender oil, Japanese peppermint oil, melissa oil, sage oil, rosemary oil, cinnamon oil and clove oil.

The controlled release insect pest repellent of the present invention thus molded in various forms may be used in the following manner depending on the form. When molded into pellets, it may be applied to the roots of trees as such so as to protect the trees from insect pests. Alternatively, it may be charged into an open vessel and hung in, for example, a porch, a lavatory, a room corner or a kennel. When molded into a sheet or a net, it may be placed in a kennel or wound around a tree. In particular, a sheet-type product may be cut into an appropriate size and provided with metal fittings so as to give a collar for a dog or cat for exterminating insect pests such as a mosquito, flea or mite. A net-type product may be used together with a window screen so as to severely prevent insect pests from entering into the interior. A rod-type product may be wound around a tree or hung at the entrance of a kennel. Furthermore, it may be used as farm materials. Namely, it may be used as supports or nets in farms to thereby protect crops from insect pests. In the field of sericulture, furthermore, invasion of insect pests or the escape of silkworms can be inhibited by covering a rearing bed with the controlled release insect pest repellent of the present invention in the form of pellets or a sheet.

To further illustrate the present invention, the following Examples will be described below, which, however do not limit the present invention in any way. Unless otherwise specified, all parts, percents, ratios and the like are by weight.

EXAMPLE 1

To 100 parts of an ethylene/vinyl acetate copolymer containing 26% of a vinyl acetate unit (trade name, Ultrathene UE 634; manufactured by Tosoh Corporation), were added 40 parts of chlorinated polyethylene (trade name, Daisolac H-135; manufactured by Osaka Soda K. K.), 40 parts of aluminum hydroxide having an average particle size of 3 μm and 10 parts of (+)-cis-p-menthane-3,8-diol which was employed as a repellent component. After uniformly mixing, the obtained mixture was kneaded in a mixing roll and formulated into a sheet-type controlled release insect pest repellent having a thickness of 1 mm. The persistence of the repellent component contained in the sheet-type insect pest repellent thus obtained was monitored with the lapse of time (25° C., 65% RH) by gas chromatography. The results are as follows.

|  | Time (month) | | | | | |
| --- | --- | --- | --- | --- | --- | --- |
|  | 0 | 1 | 3 | 6 | 9 | 12 |
| Persistence (%) | 100.0 | 92.7 | 70.7 | 59.5 | 59.1 | 58.9 |

EXAMPLE 2

The procedure of Example 1 was repeated except that the (+)-cis-p-menthane-3,8-diol was replaced with a mixture (1:1) of (+)-cis-p-menthane-3,8-diol and (−)-trans-p-menthane-3,8-diol to thereby give a sheet-type controlled release insect pest repellent having a thickness of 1 mm. The persistence of the repellent components contained therein was monitored with the lapse of time (25° C., 65% RH) by gas chromatography. The results are as follows.

|  | Time (month) | | | | | |
| --- | --- | --- | --- | --- | --- | --- |
|  | 0 | 1 | 3 | 6 | 9 | 12 |
| Persistence (%) | 100.0 | 85.4 | 68.3 | 51.6 | 39.4 | 27.2 |

EXAMPLE 3

To 100 parts of an ethylene/vinyl acetate copolymer containing 26% of a vinyl acetate unit (trade name, Ultrathene UE 634; manufactured by Tosoh Corporation), were added 20 parts of an ethylene/vinyl acetate copolymer containing 60% of a vinyl acetate unit (trade name, Soarblen CI; manufactured by Nippon Synthetic Chemical Industry, Co., Ltd.) and 10 parts of a mixture (1:1) of (+)-cis-p-menthane-3,8-diol and (−)-trans-p-menthane-3,8-diol. After uniformly mixing, the obtained mixture was kneaded in a mixing roll and formulated into a sheet-type controlled release insect pest repellent having a thickness of 1 mm. The persistence of the repellent components contained in the sheet-type insect pest repellent thus obtained was monitored with the lapse of time (25° C., 65% RH) by gas chromatography. The results are as follows.

|  | Time (month) | | | | | |
| --- | --- | --- | --- | --- | --- | --- |
|  | 0 | 1 | 3 | 6 | 9 | 12 |
| Persistence (%) | 100.0 | 90.3 | 66.0 | 60.7 | 56.5 | 52.1 |

The results of these Examples indicate the following facts. The controlled release insect pest repellent of Example 1 wherein an isomer of p-menthane-3,8-diol was blended alone with an ethylene/vinyl acetate copolymer base showed continuous release of the repellent component by portions for approximately 6 months. The controlled release insect pest repellents of Examples 2 and 3, each contained a liquid mixture of cis- and trans-isomers of p-menthane-3,8-diol as repellent components, showed continuous release of the repellent components by portions for approximately 12 months. Thus, it is understood that stable controlled release systems may be readily formed in the latter cases, compared with the one of Example 1 containing a single p-menthane-3,8-diol isomer.

EXAMPLE 4

To 100 parts of an ethylene/vinyl acetate copolymer containing 26% of a vinyl acetate unit (trade name, Ultrathene UE 634; manufactured by Tosoh Corporation), was added 15 parts of a mixture (2:1) of (−)-cis-p-menthane-3,8-diol and (+)-trans-p-menthane-3,8-diol which were employed as repellent components. After uniformly mixing, the obtained mixture was kneaded in a mixing roll and formulated into a sheet-type controlled release insect pest repellent having a thickness of 1 mm. The persistence of the repellent component contained in the sheet-type insect pest repellent thus obtained was monitored with the lapse of time by gas chromatography. The results are as follows.

|  | Time (month) | | | | | |
| --- | --- | --- | --- | --- | --- | --- |
|  | 0 | 1 | 3 | 6 | 9 | 12 |
| Persistence (%) | 100.0 | 93.5 | 81.2 | 68.4 | 60.1 | 57.8 |

EXAMPLE 5

To 100 parts of an ethylene/vinyl acetate copolymer containing 26% of a vinyl acetate unit (trade name, Ultrathene UE 634; manufactured by Tosoh Corporation), were added 30 parts of an ethylene/vinyl acetate copolymer containing 60% of a vinyl acetate unit (trade name, Soarblen CI; manufactured by Nippon Synthetic Chemical Industry Co., Ltd.) and 30 parts of a mixture (2:1) of (+)-cis-p-menthane-3,8-diol and (−)-trans-p-menthane-3,8-diol. After uniformly mixing, the obtained mixture was kneaded in a mixing roll and formulated into a sheet-type controlled release insect pest repellent having a thickness of 2 mm. The repellent effect of the sheet-type insect pest repellent thus obtained was examined by the following method using fleas.

The sheet was cut into square pieces of a width of 10 mm and provided with metallic fittings so as to give a collar for a dog. For comparison, a sheet having a thickness of 2 mm was prepared by using the same materials except for the repellent components, and similarly formulated into a collar for a dog. Each dog collar was allowed to stand under open-air conditions at room temperature for a definite period. Then, each collar was put on a dog for a week and the time required that the repellent effect made fleas in the hair of the dog migrate onto the surface of the hair was determined. When fleas completely migrated to the surface of the hair, the dog was brushed so as to remove the fleas. One week after the application of the collar, the conditions were observed again.

The persistence of the repellent component contained in the sheet-type insect pest repellent thus obtained with the lapse of time as well as the repellent effect thereof on fleas are as follows.

Change in persistence with the lapse of time:

|  | Time (month) | | | |
| --- | --- | --- | --- | --- |
|  | 0 | 1 | 3 | 6 |
| Persistence (%) | 100.0 | 94.2 | 84.0 | 72.0 |

Time required for migration of fleas from the skin to the surface of the hair:

|  | Time (month) | | | |
| --- | --- | --- | --- | --- |
|  | 0 | 1 | 3 | 6 |
| Example | 1 hour | 1 hour | 1.5 hours | 2 hours |
| Comparative Example | No migration | No migration | No migration | No migration |

Conditions 1 week after application of collar:

|  | Time (month) | | | |
| --- | --- | --- | --- | --- |
|  | 0 | 1 | 3 | 6 |
| Example | No fleas | No fleas | No fleas | No fleas |
| Comparative Example | Fleas in hair | Fleas in hair | Fleas in hair | Fleas in hair |

Thus, the collar containing the repellent components, which had been allowed to stand for 6 months under open-air conditions, made fleas in the hair of the dog completely migrate onto the surface of the hair within 2 hours. Thus, it was proved that the repellent effect was controlled for a long time.

While the invention has been described in detail and with reference to specific embodiments thereof, it will be apparent to one skilled in the art that various changes and modifications can be made therein without departing from the spirit and scope thereof.

What is claimed is:

1. A controlled release insect pest repellent comprising p-menthane-3,8-diol with an ethylene/vinyl acetate copolymer, wherein said ethylene vinyl acetate copolymer contains a vinyl acetate unit at a content of approximately from 15 to 40% by weight.

2. A controlled release insect pest repellent as claimed in claim 1, wherein said p-menthane-3,8-diol is contained in an amount of approximately from 5 to 30% by weight.

3. A controlled release insect pest repellent as claimed in claim 1, wherein said p-menthane-3,8-diol is a mixture of cis- and trans-isomers thereof at such a ratio as to make said mixture liquid at room temperature.

4. A controlled release insect pest repellent as claimed in claim 3, wherein the content of p-menthane-3,8-diol is 10 to 20% by weight.

* * * * *